United States Patent
Rabiner et al.

(10) Patent No.: US 6,733,451 B2
(45) Date of Patent: May 11, 2004

(54) APPARATUS AND METHOD FOR AN ULTRASONIC PROBE USED WITH A PHARMACOLOGICAL AGENT

(75) Inventors: Robert A. Rabiner, North Reading, MA (US); Bradley A. Hare, Chelmsford, MA (US); Rebecca I. Marciante, North Reading, MA (US); Elaine S. Buffen, Westborough, MA (US); Mark R. Gosnell, Weston, MA (US); Heather L. Senseney-Mellor, Durham, NH (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 0 days.

(21) Appl. No.: 10/396,914

(22) Filed: Mar. 25, 2003

(65) Prior Publication Data

US 2003/0181812 A1 Sep. 25, 2003

Related U.S. Application Data

(63) Continuation-in-part of application No. 10/373,134, filed on Feb. 24, 2003, which is a continuation of application No. 09/784,619, filed on Feb. 15, 2001, now Pat. No. 6,524,251, which is a continuation-in-part of application No. 09/618,352, filed on Jul. 19, 2000, now Pat. No. 6,551,337.

(60) Provisional application No. 60/178,901, filed on Jan. 28, 2000, and provisional application No. 60/157,824, filed on Oct. 5, 1999.

(51) Int. Cl.[7] .................................................. A61B 8/12
(52) U.S. Cl. .................. 600/439; 600/459; 600/462; 600/471; 600/463; 600/466; 604/20; 604/21; 604/22; 604/169; 606/169; 606/159; 606/167; 606/171
(58) Field of Search ................................ 600/459, 439, 600/462–464, 466–467, 471–472; 604/20–22; 606/169–171, 159, 167

(56) References Cited

U.S. PATENT DOCUMENTS

| | | | | |
|---|---|---|---|---|
| 2,990,616 A | 7/1961 | Balamuth et al. | ............ | 433/119 |
| 3,526,219 A | 9/1970 | Balamuth | .................... | 600/565 |
| 3,565,062 A | 2/1971 | Kuris | ......................... | 606/169 |
| 3,589,363 A | 6/1971 | Banko | .......................... | 604/22 |
| 3,805,787 A | 4/1974 | Banko | .......................... | 604/22 |
| 3,861,391 A | 1/1975 | Antonevich et al. | ......... | 606/128 |

(List continued on next page.)

FOREIGN PATENT DOCUMENTS

| | | | | |
|---|---|---|---|---|
| EP | 0293472 | 12/1988 | ............ | A61B/17/22 |
| EP | 0541249 | 5/1993 | ............ | A61F/9/007 |
| WO | WO 90/01300 | 2/1990 | ............ | A61B/17/32 |
| WO | WO 95/03740 | 2/1995 | ............ | A61B/17/20 |
| WO | WO 96/07377 | 3/1996 | ............ | A61F/9/007 |
| WO | WO 98/35721 | 8/1998 | ............ | A61B/17/22 |
| WO | WO 98/55032 | 12/1998 | ............ | A61B/17/22 |
| WO | WO 99/33404 | 7/1999 | ............ | A61F/9/007 |
| WO | WO 99/35982 | 7/1999 | ............ | A61B/17/32 |
| WO | WO 00/21444 | 4/2000 | ............ | A61B/17/20 |

OTHER PUBLICATIONS

PCT International Search Report for International Application No. PCT/US02/22517 dated Oct. 18, 2002.

*Primary Examiner*—Shawntina Fuqua
(74) *Attorney, Agent, or Firm*—Palmer & Dodge, LLP; Richard B. Smith; David J. Dykeman

(57) ABSTRACT

The present invention provides an apparatus and a method of using an ultrasonic probe with a pharmacological agent to enhance an occlusion treating effect of the ultrasonic probe to effectively remove an occlusion. The pharmacological agent is released through a catheter to treat the occlusion and enhance an effect of a transverse ultrasonic vibration of the ultrasonic probe to effectively remove the occlusion. The pharmacological agent continues to travel downstream of the site of the occlusion and work in conjunction with the ultrasonic probe to reduce the occlusion to a size that can easily be removed from the body naturally in order to prevent reformation of the occlusion and other health risks.

68 Claims, 6 Drawing Sheets

U.S. PATENT DOCUMENTS

| | | | | |
|---|---|---|---|---|
| 4,136,700 | A | 1/1979 | Broadwin et al. | 606/169 |
| 4,236,510 | A | 12/1980 | Hatter et al. | 601/2 |
| 4,474,180 | A | 10/1984 | Angulo | 128/328 |
| 4,486,680 | A | 12/1984 | Bonnet et al. | 310/323.19 |
| 4,493,694 | A | 1/1985 | Wuchinich | 604/22 |
| 4,504,264 | A | 3/1985 | Kelman | 604/22 |
| 4,526,571 | A | 7/1985 | Wuchinich | 604/22 |
| 4,535,759 | A | 8/1985 | Polk et al. | 128/24 A |
| 4,634,420 | A | 1/1987 | Spinosa et al. | 604/22 |
| 4,838,853 | A | 6/1989 | Parisi | 604/22 |
| 4,867,141 | A | 9/1989 | Nakada et al. | 601/4 |
| 4,870,953 | A * | 10/1989 | DonMicheal et al. | 606/128 |
| 4,886,491 | A | 12/1989 | Parisi et al. | 304/22 |
| 4,920,954 | A | 5/1990 | Alliger et al. | 128/24 A |
| 4,922,902 | A | 5/1990 | Wuchinich et al. | 604/22 |
| 4,931,047 | A | 6/1990 | Broadwin et al. | 604/22 |
| 4,961,424 | A | 10/1990 | Kubota et al. | 128/24 A |
| 4,962,755 | A | 10/1990 | King et al. | 601/2 |
| 4,989,583 | A | 2/1991 | Hood | 128/24 A |
| 5,015,227 | A | 5/1991 | Broadwin et al. | 604/22 |
| 5,017,379 | A | 5/1991 | Lemelson | 424/450 |
| 5,026,387 | A | 6/1991 | Thomas | 606/169 |
| 5,057,119 | A | 10/1991 | Clark et al. | 606/169 |
| 5,057,182 | A | 10/1991 | Wuchinich | 156/580.1 |
| 5,059,210 | A | 10/1991 | Clark et al. | 606/169 |
| 5,062,827 | A | 11/1991 | Wiksell | 604/22 |
| 5,106,741 | A | 4/1992 | Marotti et al. | 435/226 |
| 5,112,300 | A | 5/1992 | Ureche | 604/22 |
| 5,116,343 | A | 5/1992 | Ams et al. | 606/128 |
| 5,163,421 | A | 11/1992 | Bernstein et al. | 128/24 |
| 5,167,619 | A | 12/1992 | Wuchinich | 604/22 |
| 5,171,387 | A | 12/1992 | Wuchinich | 156/73.3 |
| 5,176,677 | A | 1/1993 | Wuchinich | 604/356 |
| 5,180,363 | A | 1/1993 | Idemoto et al. | 202/32 |
| 5,190,517 | A | 3/1993 | Zieve et al. | 604/22 |
| 5,221,282 | A | 6/1993 | Wuchinich | 606/99 |
| 5,243,997 | A | 9/1993 | Uflacker et al. | 600/565 |
| 5,267,954 | A | 12/1993 | Nita | 604/22 |
| 5,269,297 | A | 12/1993 | Weng et al. | 128/24 AA |
| 5,271,735 | A | 12/1993 | Greenfeld et al. | 604/266 |
| 5,300,021 | A | 4/1994 | Wuchinich | 604/22 |
| 5,304,115 | A | 4/1994 | Pflueger et al. | 604/22 |
| 5,312,328 | A | 5/1994 | Nita et al. | 604/22 |
| 5,312,329 | A | 5/1994 | Beaty et al. | 604/22 |
| 5,324,299 | A | 6/1994 | Davison et al. | 606/167 |
| 5,334,183 | A | 8/1994 | Wuchinich | 606/46 |
| 5,342,292 | A | 8/1994 | Nita et al. | 604/22 |
| 5,358,505 | A | 10/1994 | Wuchinich | 606/99 |
| 5,366,490 | A | 11/1994 | Edwards et al. | 607/99 |
| 5,368,558 | A | 11/1994 | Nita | 604/22 |
| 5,380,274 | A | 1/1995 | Nita | 604/22 |
| 5,382,228 | A | 1/1995 | Nita et al. | 604/22 |
| 5,397,293 | A | 3/1995 | Alliger et al. | 601/2 |
| 5,397,301 | A | 3/1995 | Pflueger et al. | 604/22 |
| 5,405,318 | A | 4/1995 | Nita | 604/22 |
| 5,417,654 | A | 5/1995 | Kelman | 604/22 |
| 5,417,672 | A | 5/1995 | Nita et al. | 604/533 |
| 5,419,761 | A | 5/1995 | Narayanan et al. | 604/22 |
| 5,427,118 | A | 6/1995 | Nita et al. | 128/772 |
| 5,447,509 | A | 9/1995 | Mills et al. | 606/1 |
| 5,458,612 | A | 10/1995 | Chin | 606/192 |
| 5,469,853 | A | 11/1995 | Law et al. | 128/662.06 |
| 5,472,441 | A | 12/1995 | Edwards et al. | 606/41 |
| 5,478,558 | A | 12/1995 | Eibl et al. | 424/94.63 |
| 5,484,398 | A | 1/1996 | Stoddard | 604/22 |
| 5,498,236 | A | 3/1996 | Dubrul et al. | 604/22 |
| 5,516,043 | A | 5/1996 | Manna et al. | 239/102.2 |
| 5,580,962 | A | 12/1996 | Eibl et al. | 530/395 |
| 5,603,445 | A | 2/1997 | Hill et al. | 228/4.5 |
| 5,628,743 | A | 5/1997 | Cimino | 606/1 |
| 5,630,837 | A | 5/1997 | Crowley | 601/2 |
| 5,672,172 | A | 9/1997 | Zupkas | 606/20 |
| 5,676,649 | A | 10/1997 | Boukhny et al. | 604/22 |
| 5,713,848 | A | 2/1998 | Dubrul et al. | 604/22 |
| 5,720,710 | A | 2/1998 | Tachibana et al. | 601/2 |
| 5,725,494 | A | 3/1998 | Brisken | 604/22 |
| 5,728,062 | A | 3/1998 | Brisken | 604/22 |
| 5,735,811 | A | 4/1998 | Brisken | 604/22 |
| 5,741,225 | A | 4/1998 | Lax et al. | 604/22 |
| 5,772,627 | A | 6/1998 | Acosta et al. | 604/22 |
| 5,827,203 | A | 10/1998 | Nita | 601/2 |
| 5,836,896 | A | 11/1998 | Rosenschein | 601/2 |
| 5,836,897 | A | 11/1998 | Sakurai et al. | 601/2 |
| 5,843,017 | A | 12/1998 | Yoon | 604/22 |
| 5,846,218 | A | 12/1998 | Brisken et al. | 604/22 |
| 5,891,149 | A | 4/1999 | Young et al. | 606/80 |
| 5,895,370 | A | 4/1999 | Edwards et al. | 604/22 |
| 5,925,016 | A | 7/1999 | Chornenky et al. | 604/96 |
| 5,931,805 | A | 8/1999 | Brisken | 604/22 |
| 5,935,096 | A | 8/1999 | Barrett | 604/22 |
| 5,935,142 | A | 8/1999 | Hood | 606/169 |
| 5,957,882 | A | 9/1999 | Nita et al. | 604/22 |
| 5,964,756 | A | 10/1999 | McGaffigan et al. | 606/41 |
| 5,989,208 | A | 11/1999 | Nita | 604/22 |
| 5,989,209 | A | 11/1999 | Barrett | 604/22 |
| 5,989,274 | A | 11/1999 | Davison et al. | 606/169 |
| 6,001,355 | A | 12/1999 | Dowdle | 424/94.64 |
| 6,032,078 | A | 2/2000 | Rudie | 607/101 |
| 6,033,375 | A | 3/2000 | Brumbach | 604/22 |
| 6,077,285 | A | 6/2000 | Boukhny | 606/169 |
| 6,083,501 | A | 7/2000 | Miyata et al. | 424/158.1 |
| 6,224,565 | B1 | 5/2001 | Cimino | 604/22 |
| 6,245,095 | B1 | 6/2001 | Dobak, III et al. | 607/105 |
| 6,277,084 | B1 | 8/2001 | Abele et al. | 601/2 |
| 6,280,413 | B1 | 8/2001 | Clark et al. | 604/104 |
| 6,287,271 | B1 * | 9/2001 | Dubrul et al. | 604/22 |
| 6,303,635 | B1 | 10/2001 | Kawai et al. | 514/325 |
| 6,364,840 | B1 | 4/2002 | Crowley | 600/463 |
| 6,462,172 | B1 | 10/2002 | Maclennan et al. | 530/326 |
| 6,508,782 | B1 | 1/2003 | Evans et al. | 604/22 |
| 6,509,348 | B1 | 1/2003 | Ogletree | 514/301 |

* cited by examiner

APPARATUS AND METHOD FOR AN ULTRASONIC PROBE USED WITH A PHARMACOLOGICAL AGENT

RELATED APPLICATIONS

This application is a continuation-in-part of application Ser. No. 10/373,134, filed Feb. 24, 2003, which is a continuation of application Ser. No. 09/784,619, filed Feb. 15, 2001, now U.S. Pat. No. 6,524,251, which is a continuation-in-part of application Ser. No. 09/618,352, filed on Jul. 19, 2000, which claims the benefit of Provisional Application Serial No. 60/178,901, filed Jan. 28, 2000, and claims the benefit of Provisional Application Serial No. 60/157,824, filed Oct. 5, 1999, the entirety of all these applications are hereby incorporated herein by reference.

FIELD OF THE INVENTION

The present invention relates to an ultrasonic medical device, and more particularly to an apparatus and method of using an ultrasonic probe with a pharmacological agent to treat an occlusion and effectively remove the occlusion and prevent subsequent occlusion formation and other health risks.

BACKGROUND OF THE INVENTION

Vascular occlusive disease affects millions of individuals worldwide and is characterized by a dangerous blockage of vasculatures. Vascular occlusive disease includes thrombosed hemodialysis grafts, peripheral artery disease, deep vein thrombosis, coronary artery disease, heart attack and stroke. Vasculatures include veins, arteries, blood vessels, intestines, ducts and other body lumens that materials may flow through. Heart attacks are an especially common vascular occlusive disease, with an approximate annual rate of 800,000 people in the United States having acute heart attacks with approximately 213,000 of those people dying. Strokes are also common, with approximately 80% of all strokes being ischemic strokes caused when a vascular occlusion formed in one part of the body travels to a smaller blood vessel in the brain and inhibits blood flow to the brain. Vascular occlusions (clots, intravascular blood clots or thrombus, occlusional deposits, such as calcium deposits, fatty deposits, atherosclerotic plaque, cholesterol buildup, fibrous material buildup, arterial stenoses) result in the restriction or blockage of blood flow in the vasculatures in which they occur. Occlusions result in oxygen deprivation ("ischemia") of tissues supplied by these blood vessels. Prolonged ischemia results in permanent damage of tissues which can lead to myocardial infarction, stroke or death. Occlusions frequently occur in coronary arteries, peripheral arteries and other blood vessels.

The disruption of an occlusion can be affected by mechanical methods, ultrasonic methods, pharmacological agents or combinations of all three. Many procedures involve inserting an insertion lumen into a vasculature of a body. Insertion lumens include, but are not limited to, probes, catheters, wires, tubes and similar devices.

Mechanical methods of treating thrombolysis include balloon angioplasty, which can result in ruptures in a blood vessel, and is generally limited to larger blood vessels. In addition, scarring of vessels is common, which may lead to the formation of a secondary occlusion (a process known as restenosis). Another common problem is secondary vasoconstriction (classic recoil), a process by which spasms or an abrupt closure of the blood vessel occurs. These problems are common in treatments employing interventional devices. In traditional angioplasty, for instance, a balloon catheter is inserted into the occlusion, and through the application of hydraulic forces in the range of about ten to about fourteen atmospheres of pressure, the balloon is inflated. The non-compressible balloon applies this significant force to compress and flatten the occlusion, thereby opening the vessel for blood flow. However, these extreme forces result in the application of extreme stresses to the vessel, potentially rupturing the vessel, or weakening it and thereby increasing the chance of post-operative aneurysm, or creating vasoconstrictive or restenotic conditions. In addition, the particulate matter forming the occlusion is not removed, rather it is just compressed. Other mechanical devices that drill through and attempt to remove an occlusion have also been used, and create the same danger of physical damage to blood vessels.

Ultrasonic probes using ultrasonic energy to fragment body tissue have been used in many surgical procedures (see, e.g., U.S. Pat. No. 5,112,300; U.S. Pat. No. 5,180,363; U.S. Pat. No. 4,989,583; U.S. Pat. No. 4,931,047; U.S. Pat. No. 4,922,902; and U.S. Pat. No. 3,805,787). Ultrasonic devices used for vascular treatments typically comprise an extracorporeal transducer coupled to a solid metal wire which is then threaded through the blood vessel and placed in contact with an occlusion (see, e.g., U.S. Pat. No. 5,269,297). In some cases, the transducer, comprising a bendable plate, is delivered to the site of the clot (see, e.g., U.S. Pat. No. 5,931,805).

Some ultrasonic devices include a mechanism for irrigating an area where the ultrasonic treatment is being performed (e.g., a body cavity or lumen) in order to wash biological material from the area of treatment. Mechanisms used for irrigation or aspiration known in the art are generally structured such that they increase the overall cross-sectional profile of the elongated probe, by including inner and outer concentric lumens within an ultrasonic probe to provide irrigation and aspiration channels. In addition to making the probe more invasive, prior art probes also maintain a strict orientation of the aspiration and the irrigation mechanism, such that the inner and outer lumens for irrigation and aspiration remain in a fixed position relative to one another, which is generally closely adjacent to the area of treatment. Thus, the irrigation lumen does not extend beyond the suction lumen (i.e., there is no movement of the lumens relative to one another) and any aspiration is limited to picking up fluid and/or tissue remnants within the defined area between the two lumens.

As discussed above, medical devices utilizing ultrasonic energy to destroy material comprising an occlusion in the human body are known in the art. A major drawback of prior art ultrasonic devices comprising a probe for occlusion removal is that the devices are relatively slow in comparison to procedures that involve surgical excision. This is mainly attributed to the fact that such ultrasonic devices rely on imparting ultrasonic energy to contacting occlusions by undergoing a longitudinal vibration of the probe tip, wherein the probe tip is mechanically vibrated at an ultrasonic frequency in a direction parallel to the probe longitudinal axis. Thus, the treatment area is localized at the probe tip, which substantially limits its ability to ablate large occlusion areas in a short time. An ultrasonic medical device with a multiple material coaxial construction for conducting axial vibrations is known in the art (see, e.g., U.S. Pat. No. 6,277,084). In addition to prior art ultrasonic devices being slow, previous ultrasonic methods of treating plaque still include many undesirable complications and dangers to the patient.

The use of a pharmacological agent alone to treat a vascular occlusion is common, but suffers from a variety of limitations that compromise the effectiveness of the removal of the vascular occlusion. It is difficult to disperse the pharmacological agent symmetrically to the vascular occlusion, thereby leaving portions of the vascular occlusion untreated. Often, portions of the vascular occlusion are carried downstream of the site of the vascular occlusion and lead to further problems including embolism. In addition, delivery of the pharmacological agent is inefficient and infusion times are long as the agent naturally dissolves into areas of the vascular occlusion. Adverse complications such as hemorrhages and bleeding are also common, thereby creating additional health risks beyond those presented by the vascular occlusion. Finally, large quantities of the pharmacological agent are needed to treat the thrombus, thereby driving up the cost of the treatment.

Prior art attempts to safely and effectively ablate an occlusion in a vasculature of a body have been less than successful. U.S. Pat. No. 6,508,782 to Evans et al. discloses a catheter for dissolving blockages in tissues. The Evans et al. device uses a catheter with an inflatable member either alone or in conjunction with a medicament for dissolving the blockages. The Evans et al. device discloses a catheter with an inflatable member near the distal tip of the catheter to prevent the blockage from passing downstream of the blockage and a perfusion channel for removal of the broken up blockage. The Evans et al. device is complicated, unreliable and necessitates a time consuming procedure that requires the exchange of various lumens to deliver the medicament and to vibrate the Evans et al. device. Since vibratory motion for the Evans et al. device is longitudinal and at a distal tip, the Evans et al. device does not focus on all parts of the blockage and does not effectively and efficiently remove the blockage. Therefore, there remains a need in the art for effectively ablating an occlusion that combines the ultrasonic energy of an ultrasonic probe with the dissolving effects of a pharmacological agent that is simple, quick, reliable, efficient, effective, does not harm healthy tissue and continues to break up particulate of the occlusion downstream to prevent occlusion formation downstream.

U.S. Pat. No. 5,925,016 to Chomenky et al. discloses a system and a method for treating thrombosis by moving drugs through the thrombus by pressure. The Chornenky et al. device isolates the thrombus by using a catheter with an occlusion balloon proximal to the thrombus, a guide wire with an occlusion placed distal to the thrombus, and an infusion catheter that delivers drugs distal to the thrombus through pressure. Since the Chomenky et al. device relies on the drug and the non-symmetric pressurized delivery of the drug to remove the thrombus, the thrombus is not effectively removed and may result in complications downstream of the thrombus. The Chornenky et al. device uses a time consuming procedure that imparts high stresses to the vessel walls that can damage the vessel. Therefore, there remains a need in the art for effectively ablating an occlusion that combines the ultrasonic energy of an ultrasonic probe with the dissolving effects of a pharmacological agent that is simple, quick, reliable, efficient, effective, does not harm healthy tissue and continues to break up particulate of the occlusion downstream to prevent occlusion formation downstream.

U.S. Pat. No. 6,280,413 to Clark et al. discloses a thrombolytic filtration and drug delivery catheter comprising a shaft and longitudinal ribs that are compressed when moved to the treatment site and expand to a diameter greater than the shaft of the catheter. In the Clark et al. device, drugs are delivered through a lumen in the catheter and are delivered through ports in the ribs. Since the Clark et al. device relies on the non-symmetric dispersion of the drug, the Clark et al. device does not effectively remove an occlusion and the occlusion can reform downstream. The Clark et al. device is complicated and relies on a separate lumen to remove the particles of the thrombus. In addition, the longitudinal ribs of the Clark et. al. device can impart high stresses to the vasculature and harm healthy tissue. Therefore, there remains a need in the art for effectively ablating an occlusion that combines the ultrasonic energy of an ultrasonic probe with the dissolving effects of a pharmacological agent that is simple, quick, reliable, efficient, effective, does not harm healthy tissue and continues to break up particulate of the occlusion downstream to prevent occlusion formation downstream.

The prior art attempts of removing an occlusion from a vasculature in a body are complicated, expensive, unsafe, ineffective, time consuming, inefficient and compromise the health of a patient by potentially allowing the occlusion to reform downstream. Therefore, there remains a need in the art for effectively ablating an occlusion that combines the ultrasonic energy of an ultrasonic probe with the dissolving effects of a pharmacological agent that is simple, quick, reliable, efficient, effective, does not harm healthy tissue and continues to break up particulate of the occlusion downstream to prevent occlusion formation downstream.

SUMMARY OF THE INVENTION

The present invention relates to an ultrasonic medical device, and more particularly to an apparatus and method of using an ultrasonic probe with a pharmacological agent to treat an occlusion and effectively remove the occlusion and prevent subsequent occlusion formation and other health risks.

The present invention is an ultrasonic medical device comprising an ultrasonic probe and a catheter surrounding a length of a longitudinal axis of the ultrasonic probe used with a pharmacological agent. In a preferred embodiment of the present invention, the catheter delivers the pharmacological agent to treat the occlusion. In a preferred embodiment of the present invention, the pharmacological agent is tissue plasminogen activator (tPA). The pharmacological agent enhances an occlusion treatment effect of the ultrasonic probe.

The present invention is an ultrasonic medical device comprising an elongated, flexible probe and a catheter surrounding a length of a longitudinal axis of the elongated, flexible probe. A pharmacological agent moves through the catheter and enhances an effect of a transverse ultrasonic vibration of the elongated, flexible probe to treat the occlusion. The transverse ultrasonic vibration of the elongated, flexible probe produces a plurality of transverse nodes and transverse anti-nodes along a portion of the longitudinal axis of the elongated, flexible probe.

The present invention provides a method of treating an occlusion through the combined effects of an ultrasonic probe and a pharmacological agent. The ultrasonic probe is inserted into a vasculature, a catheter is delivered over a length of a longitudinal axis of the ultrasonic probe and a pharmacological agent is released through the catheter. A section of the longitudinal axis of the ultrasonic probe is exposed to the occlusion and an ultrasonic energy source is activated. The pharmacological agent continues to move downstream of a site of the occlusion to work in conjunction with the ultrasonic probe to reduce the occlusion to a size that can easily be removed from the body in conventional ways or simply dissolve into the blood stream.

The present invention provides a method of removing an occlusion by moving an elongated, flexible probe through a vasculature to a site of an occlusion, releasing a pharmacological agent in the vasculature and activating an ultrasonic energy source to vibrate a longitudinal axis of the ultrasonic probe. The pharmacological agent enhances an occlusion destroying effect of the elongated, flexible probe.

The present invention is an ultrasonic medical device and a pharmacological agent used together to treat an occlusion and efficiently remove the occlusion to prevent subsequent reformation of the occlusion and other health risks. The present invention provides an apparatus and a method for more completely removing an occlusion that is safe, simple, efficient, effective, user-friendly, reliable and cost effective.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

Figure 1:
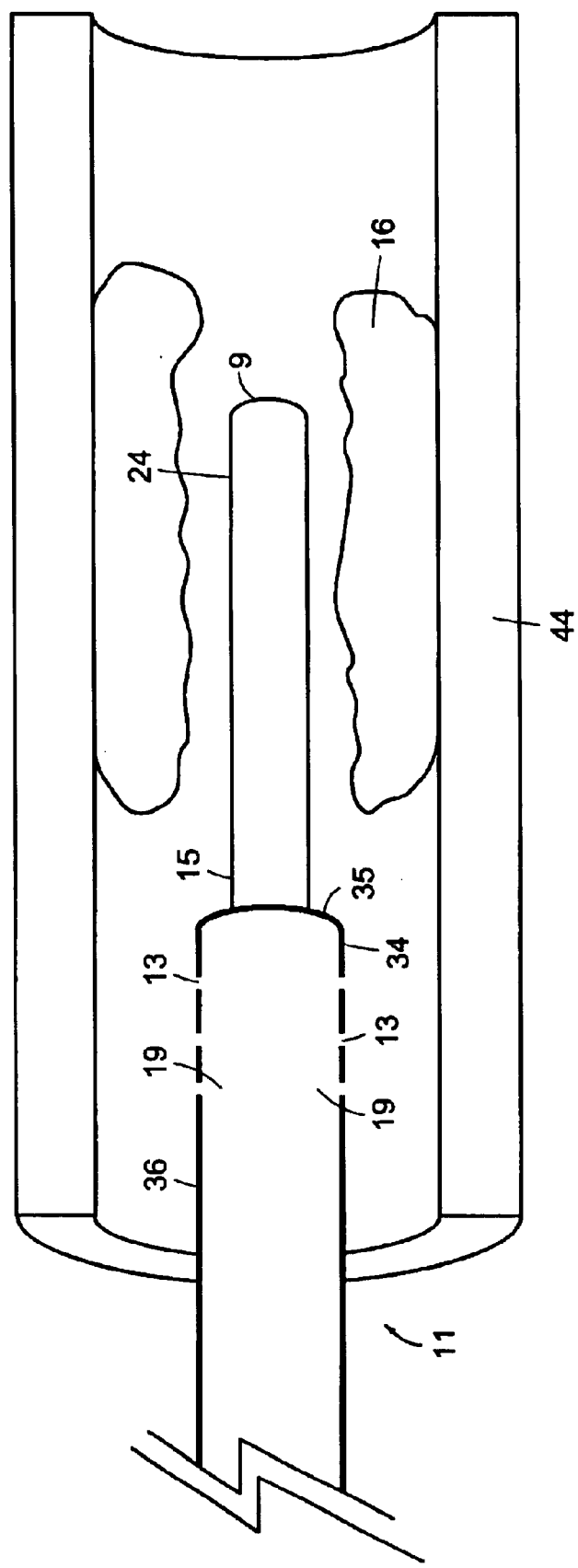
FIG. 1 shows a longitudinal cross section of a vasculature showing an ultrasonic medical device of the present invention capable of operating in a transverse mode inserted into the vasculature to treat an occlusion.

While the above-identified drawings set forth preferred embodiments of the present invention, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and spirit of the principles of the present invention.

DETAILED DESCRIPTION

The present invention provides an apparatus and a method of using an ultrasonic probe with a pharmacological agent to enhance an occlusion treating effect of the ultrasonic probe to effectively remove an occlusion. The pharmacological agent treats the occlusion at the site of the occlusion and continues to travel downstream to further break up a particulate from the occlusion into an aggregate with a size smaller than the particulate. In a preferred embodiment of the present invention, the pharmacological agent is tissue plasminogen activator (tPA).

The following terms and definitions are used herein:

"Ablate" as used herein refers to removing, clearing, destroying or taking away a biological material. "Ablation" as used herein refers to a removal, clearance, destruction, or taking away of the biological material.

"Node" as used herein refers to a region of a minimum energy emitted by an ultrasonic probe at or proximal to a specific location along a longitudinal axis of the ultrasonic probe.

"Anti-node" as used herein refers to a region of a maximum energy emitted by an ultrasonic probe at or proximal to a specific location along a longitudinal axis of the ultrasonic probe.

"Probe" as used herein refers to a device capable of propagating an energy emitted by the ultrasonic energy source along a longitudinal axis of the ultrasonic probe, resolving the energy into an effective cavitational energy at a specific resonance (defined by a plurality of nodes and a plurality of anti-nodes along an "active area" of the probe) and is capable of an acoustic impedance transformation of ultrasound energy to a mechanical energy.

"Transverse" as used herein refers to a vibration of a probe not parallel a longitudinal axis of the probe. A "transverse wave" as used herein is a wave propagated along the probe in which a direction of a disturbance at a plurality of points of a medium is not parallel to a wave vector.

"Biological material" as used herein refers to a collection of a matter including, but not limited to, a group of similar cells, intravascular blood clots or thrombus, fibrin, calcified plaque, calcium deposits, occlusional deposits, atherosclerotic plaque, fatty deposits, adipose tissues, atherosclerotic cholesterol buildup, fibrous material buildup, arterial stenoses, minerals, high water content tissues, platelets, cellular debris, wastes and other occlusive materials.

"Occlusion" as used herein refers to a blockage, a clot, a buildup or a deposit of a matter that results in an obstruction, restriction, obstruction, constriction, blockage or closure at a site of the occlusion.

"Particulate" as used herein refers to a smaller portion separated from a larger occlusion and distinct from the occlusion.

"Aggregate" as used herein refers to a smaller portion separated from a particulate that is distinct from the particulate.

FIG. 1 illustrates a section of an ultrasonic medical device 11 of the present invention proximal to an occlusion 16 inside a vasculature 44. The ultrasonic medical device 11 includes an ultrasonic probe 15 with a probe tip 9 at a distal end 24 of the ultrasonic probe 15. A catheter 36 (shown in a retracted position) surrounds a length of a longitudinal axis of the ultrasonic probe 15 and comprises a plurality of fenestrations 13 spaced circumferentially along a length of the catheter 36. In a preferred embodiment of the present invention, the plurality of fenestrations 13 are located at a distal end 34 of the catheter 36. A pharmacological agent moves through an open area 19 between the ultrasonic probe 15 and the catheter 36.

In a preferred embodiment of the present invention, the pharmacological agent moves through the plurality of fenestrations 13 at the distal end 34 of the catheter 36. The catheter 36 with the plurality of fenestrations 13 allows for the pharmacological agent to uniformly engage the occlusion 16 as the pharmacological agent moves in a radial direction through the plurality of fenestrations 13. In another embodiment of the present invention, the pharmacological agent moves through an opening 35 at a distal end 34 of the catheter 36. In another embodiment of the present invention, the pharmacological agent moves through one fenestration 13 at a position along the longitudinal axis of the catheter 36. Those skilled in the art will recognize a pharmacological agent can be moved through a catheter to engage an occlusion in many ways known in the art and be within the spirit and scope of the present invention.

Figure 2:
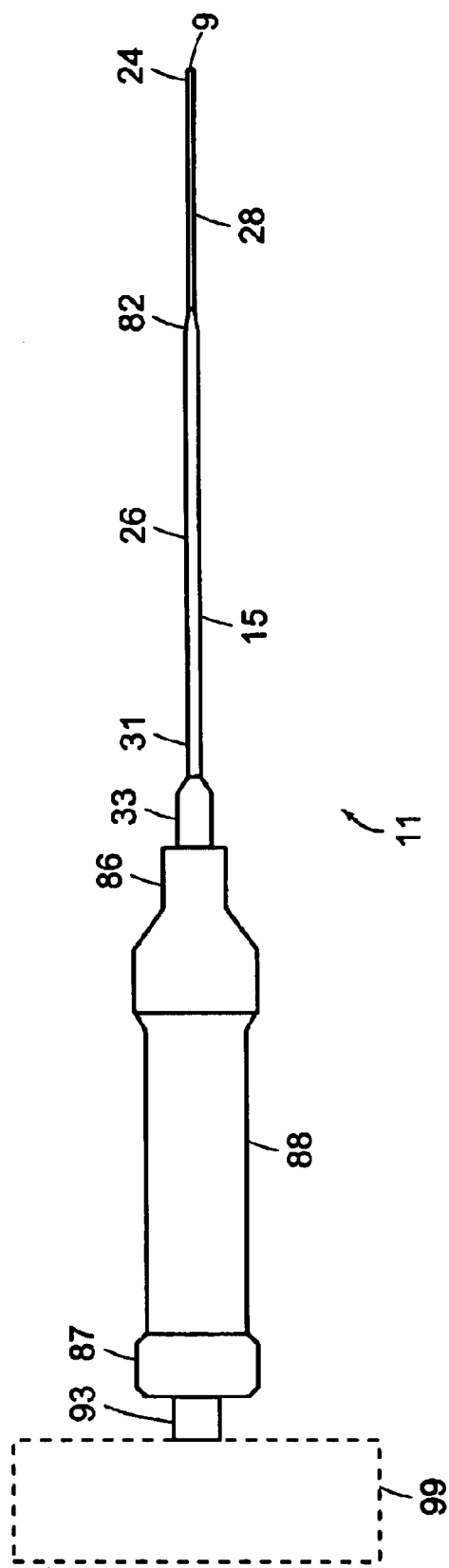
FIG. 2 shows a side plan view of an ultrasonic medical device of the present invention capable of operating in a transverse mode.

FIG. 2 shows the ultrasonic medical device 11 of the present invention. The ultrasonic medical device 11 includes the ultrasonic probe 15 which is coupled to an ultrasonic energy source or generator 99 (shown in phantom in FIGS. 2–4) for the production of an ultrasonic energy. A handle 88, comprising a proximal end 87 and a distal end 86, surrounds a transducer within the handle 88. The transducer having a first end engaging the ultrasonic energy source 99 and a second end engaging a proximal end 31 of the ultrasonic probe 15 transmits an ultrasonic energy to the ultrasonic probe 15. A connector 93 engages the ultrasonic energy source 99 to the transducer within the handle 88. The ultrasonic probe 15 includes the proximal end 31 and the distal end 24 that ends in the probe tip 9. A diameter of the ultrasonic probe 15 decreases from a first defined interval 26 to a second defined interval 28 along the longitudinal axis of the ultrasonic probe 15 over an at least one diameter transition 82. A quick attachment-detachment system 33 that engages the proximal end 31 of the ultrasonic probe 15 to the transducer within the handle 88 is illustrated generally in FIG. 2. An ultrasonic probe device with a rapid attachment and detachment means is described in the Assignee's co-pending patent applications U.S. Ser. No. 09/975,725; U.S. Ser. No. 10/268,487; U.S. Ser. No. 10/268,843, which further describe the quick attachment-detachment (QAD) system and the entirety of these applications are hereby incorporated herein by reference.

Figure 3:
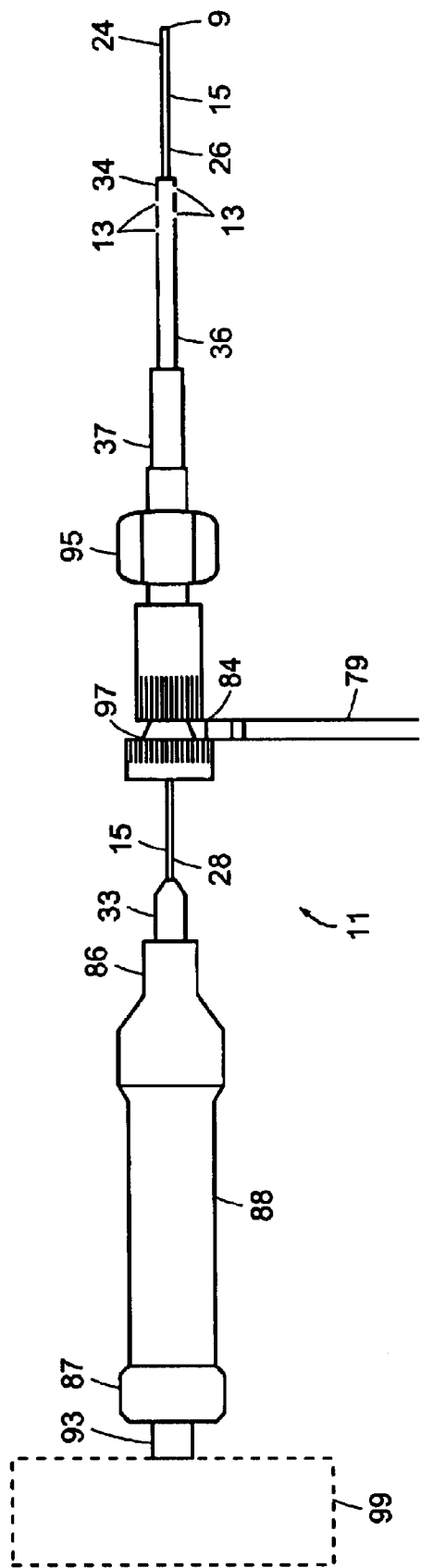
FIG. 3 shows a side plan view of an ultrasonic medical device of the present invention capable of operating in a transverse mode with a catheter surrounding a length of a longitudinal axis of an ultrasonic probe.

FIG. 3 shows the ultrasonic medical device 11 with a catheter 36 surrounding a length of the longitudinal axis of the ultrasonic probe 15. The catheter 36 comprises a proximal end 37, a distal end 34 and the plurality of fenestrations 13 along a longitudinal axis of the catheter 36. In the embodiment of the present invention shown in FIG. 3, the catheter 36 includes a port 84, a one or more placement wings 95 and a one or more valves 97. A connective tubing 79 engages the catheter 36 at the port 84 and the connective tubing 79 can be opened or closed with one or more valves 97. The catheter 36 comprises the one or more placement wings 95 to assist in the placement of the catheter 36.

The catheter 36 is a thin, flexible, hollow tube that is small enough to be threaded through a vein or an artery to deliver fluids into or withdraw fluids from a body. The catheter 36 provides a pathway for drugs, nutrients or blood products. Patients generally do not feel the movement of the catheter 36 through their body. Once in place, the catheter 36 allows a number of tests or other treatment procedures to be performed. Those skilled in the art will recognize that many catheters known in the art can be used with the present invention and still be within the spirit and scope of the present invention.

The catheter 36 of the ultrasonic medical device 11 surrounds a length of the longitudinal axis of the ultrasonic probe 15. In an embodiment of the present invention shown in FIG. 3, the catheter 36 spans a length of the ultrasonic probe 15 along the first defined interval 26 and the second defined interval 28. In another embodiment of the present invention, the catheter 36 spans a length of the ultrasonic probe 15 along the second defined interval 28. In another embodiment of the present invention, the catheter 36 spans a length of the ultrasonic probe 15 along the first defined interval 26. Those skilled in the art will recognize the catheter 36 can span any length of the ultrasonic probe 15 and be within the spirit and scope of the present invention.

The probe tip 9 can be any shape including, but not limited to, bent, a ball or larger shapes. In one embodiment of the present invention, the ultrasonic energy source 99 is a physical part of the ultrasonic medical device 11. In another embodiment of the present invention, the ultrasonic energy source 99 is not a physical part of the ultrasonic medical device 11.

The handle 88 surrounds the transducer located between the proximal end 31 of the ultrasonic probe 15 and the connector 93. In a preferred embodiment of the present invention, the transducer includes, but is not limited to a horn, an electrode, an insulator, a backnut, a washer, a piezo microphone, and a piezo drive. The transducer converts electrical energy provided by the ultrasonic energy source 99 to mechanical energy. The transducer transmits ultrasonic energy received from the ultrasonic energy source 99 to the ultrasonic probe 15. Energy from the ultrasonic energy source 99 is transmitted along the longitudinal axis of the ultrasonic probe 15, causing the ultrasonic probe 15 to vibrate in a transverse mode. The transducer is capable of engaging the ultrasonic probe 15 at the proximal end 31 with sufficient restraint to form an acoustical mass that can propagate the ultrasonic energy provided by the ultrasonic energy source 99.

The ultrasonic probe 15 has a stiffness that gives the ultrasonic probe 15 a flexibility so it can be articulated in the vasculature 44 of the body. In a preferred embodiment of the present invention shown in FIG. 1, the ultrasonic probe 15 is a wire. In a preferred embodiment of the present invention shown in FIG. 1, the diameter of the ultrasonic probe 15 decreases from the first defined interval 26 to the second defined interval 28. In another embodiment of the present invention, the diameter of the ultrasonic probe 15 decreases at greater than two defined intervals. In a preferred embodiment of the present invention, the diameter transitions 82 of the ultrasonic probe 15 are tapered to gradually change the diameter from the proximal end 31 to the distal end 24 along the longitudinal axis of the ultrasonic probe 15. In another embodiment of the present invention, the diameter transitions 82 of the ultrasonic probe 15 are stepwise to change the diameter from the proximal end 31 to the distal end 24 along the longitudinal axis of the ultrasonic probe 15. Those skilled in the art will recognize that there can be any number of defined intervals and diameter transitions and that the diameter transitions can be of any shape known in the art and be within the spirit and scope of the present invention.

In a preferred embodiment of the present invention shown in FIG. 2, a cross section of the ultrasonic probe 15 is circular. In other embodiments of the present invention, the shape of the cross section of the ultrasonic probe 15 includes, but is not limited to, square, trapezoidal, oval, triangular, circular with a flat spot and similar cross sections. Those skilled in the art will recognize that other cross sectional geometric configurations known in the art would be within the spirit and scope of the present invention.

The pharmacological agent is advanced through the connective tubing 79, the one or more valves 97 are opened and the pharmacological agent moves through the catheter 36 and out the plurality of fenestrations 13. In a preferred embodiment of the invention, the pharmacological agent moves through the plurality of fenestrations 13 along the length of the catheter 36 and is approximately uniformly distributed to the occlusion 16. In a preferred embodiment of the present invention, the occlusion 16 comprises a biological material. In a preferred embodiment of the present invention, the occlusion 16 is a vascular occlusion 16. The movement of the pharmacological agent allows the pharmacological agent to become localized at the occlusion 16 in an approximately uniform distribution to the occlusion 16. The pharmacological agent treats the occlusion 16 at the site of the occlusion 16 and enhances an occlusion treating effect of the ultrasonic probe 15. After the pharmacological agent is distributed to the occlusion 16, the ultrasonic energy source 99 is activated and energy is transmitted along the longitudinal axis of the ultrasonic probe 15 and the ultrasonic probe 15 vibrates in a transverse mode.

The transverse mode of vibration of the ultrasonic probe 15 according to the present invention differs from an axial (or longitudinal) mode of vibration disclosed in the prior art. Rather than vibrating in an axial direction, the ultrasonic probe 15 of the present invention vibrates in a direction transverse (not parallel) to the axial direction. As a consequence of the transverse vibration of the ultrasonic probe 15, the occlusion destroying effects of the ultrasonic medical device 11 are not limited to those regions of the ultrasonic probe 15 that may come into contact with the occlusion 16. Rather, as a section of the longitudinal axis of the ultrasonic probe 15 is positioned in proximity to an occlusion, a diseased area or lesion, the occlusion 16 is removed in all areas adjacent to a plurality of energetic transverse nodes and transverse anti-nodes that are produced along a portion of the longitudinal axis of the ultrasonic probe 15, typically in a region having a radius of up to about 6 mm around the ultrasonic probe 15.

Transversely vibrating ultrasonic probes for occlusion treatment are described in the Assignee's co-pending patent applications U.S. Ser. No. 09/776,015; U.S. Ser. No. 09/618, 352; and U.S. Ser. No. 09/917,471, which further describe the design parameters for such an ultrasonic probe and its use in ultrasonic devices for a treatment, and the entirety of these applications are hereby incorporated herein by reference.

Figure 4:
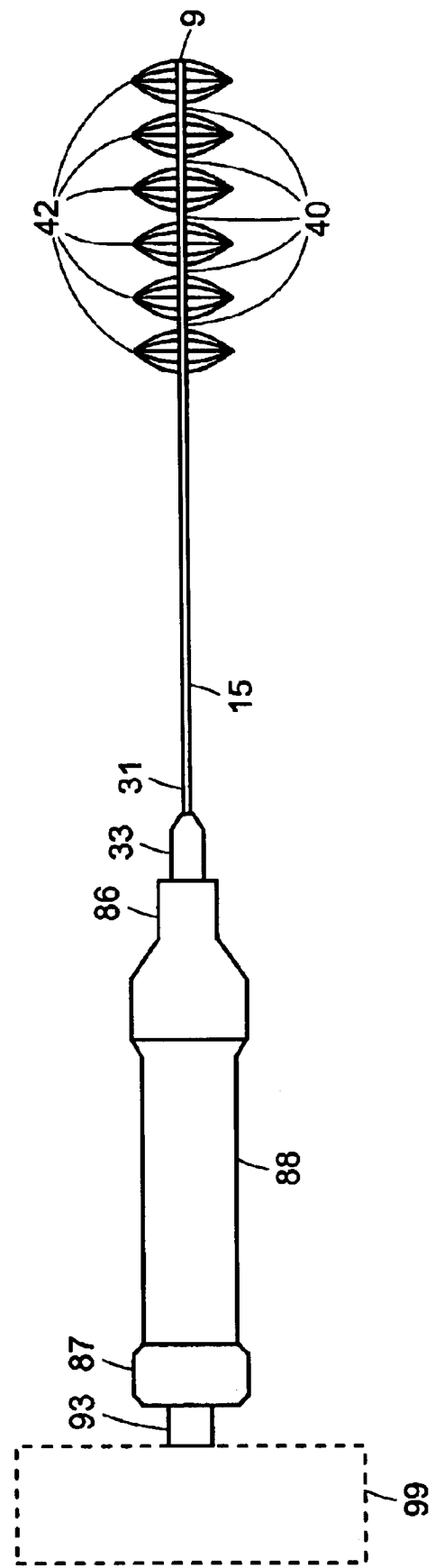
FIG. 4 shows a side plan view of an alternative embodiment of an ultrasonic medical device of the present invention showing a plurality of transverse nodes and a plurality of transverse anti-nodes along a portion of a longitudinal axis of the ultrasonic probe.

FIG. 4 illustrates an alternative embodiment of the ultrasonic medical device 11 wherein the ultrasonic probe 15 comprises an approximately uniform diameter. The ultrasonic probe 15 comprises a plurality of transverse nodes 40 and transverse anti-nodes 42 at repeating intervals along a portion of the longitudinal axis of the ultrasonic probe 15.

A length and the cross section of the ultrasonic probe 15 are sized to support the transverse ultrasonic vibration with a plurality of transverse nodes 40 and transverse anti-nodes 42 along the portion of the longitudinal axis of the ultrasonic probe 15. In a preferred embodiment of the present invention, more than one of the plurality of transverse anti-nodes 42 are in communication with the occlusion 16. The transverse ultrasonic vibration produces the plurality of transverse nodes 40 and transverse anti-nodes 42 along the portion of the longitudinal axis of the ultrasonic probe 15. The transverse nodes 40 are areas of minimum energy and minimum vibration. A plurality of transverse anti-nodes 42, or areas of maximum energy and maximum vibration, also occur at repeating intervals along the portion of the longitudinal axis of the ultrasonic probe 15. The number of transverse nodes 40 and transverse anti-nodes 42, and the spacing of the transverse nodes 40 and transverse anti-nodes 42 of the ultrasonic probe 15 depend on the frequency of the energy produced by the ultrasonic energy source 99. The separation of the transverse nodes 40 and the transverse anti-nodes 42 is a function of the frequency, and can be affected by tuning the ultrasonic probe 15. In a properly tuned ultrasonic probe 15, the transverse anti-nodes 42 will be found at a position exactly one-half of the distance between the transverse nodes 40 located adjacent to each side of the transverse anti-nodes 42.

As a consequence of the transverse vibration of the ultrasonic probe 15, the occlusion destroying effects of the ultrasonic medical device 11 are not limited to those regions of the probe 15 that may come into contact with the occlusion 16. Rather, as the ultrasonic probe 15 is swept through an area of the occlusion 16, preferably in a windshield-wiper fashion, the occlusion 16 is removed in all areas adjacent to the plurality of transverse anti-nodes 42 being produced along the portion of the longitudinal axis of the ultrasonic probe 15. The extent of a cavitational energy produced by the ultrasonic probe 15 is such that the cavitational energy extends radially outward from the longitudinal axis of the ultrasonic probe 15 at the transverse anti-nodes 42 along the longitudinal axis of the ultrasonic probe 15. In this way, actual treatment time using the transverse mode ultrasonic medical device 11 according to the present invention is greatly reduced as compared to methods disclosed in the prior art that primarily utilize longitudinal vibration (along the axis of the ultrasonic probe) for treatment of the occlusion. Utilizing longitudinal vibration limits treatment to the tip of the probe in prior art devices.

The use of the pharmacological agent in combination with the transverse vibration of the ultrasonic probe 15 enhances the occlusion treating effect of the present invention, causing the occlusion 16 to be broken up into a particulate. Some of the occlusion 16 may be completely removed from the vasculature 44 at the site of the occlusion 16 while some may reside in the vasculature 44 as a particulate downstream of the site of the occlusion 16. Sizes of the particulate vary from a small size that can be easily absorbed and discharged through the body in conventional ways to a size that may have a risk of a subsequent occlusion 16 formation downstream. The pharmacological agent treats the occlusion 16 and a portion of the occlusion 16 may be removed while the particulate is created. The removal of the occlusion 16 and the breaking up of the occlusion 16 into the particulate is done through a generation of multiple cavitational transverse anti-nodes 42 along the portion of the longitudinal axis of the ultrasonic probe 15 not parallel to the longitudinal axis of the ultrasonic probe 15. Since substantially larger affected areas can be denuded of the occlusion 16 in a short time, actual treatment time using the transverse mode ultrasonic medical device 11 according to the present invention is greatly reduced as compared to methods using prior art probes that primarily utilize longitudinal vibration (along the axis of the probe) for ablation. A distinguishing feature of the present invention is the ability to utilize ultrasonic probes 15 of extremely small diameter compared to prior art probes, without loss of efficiency, because the occlusion fragmentation process is not dependent on the area of the probe tip 9. Highly flexible ultrasonic probes 15 can therefore be designed to mimic device shapes that enable facile insertion into occlusion spaces or extremely narrow interstices that contain the material comprising the occlusion 16. Another advantage provided by the present invention is the ability to remove the occlusion 16 from large areas within cylindrical or tubular surfaces.

The pharmacological agent continues to travel downstream of the site of the occlusion 16 and continues to treat the particulate. The sizes of the particulate that are created by the fragmentation of the occlusion 16 may cause a formation of an occlusion 16 downstream from the treatment site. With the ultrasonic energy source 99 activated and the pharmacological agent continuing to travel downstream of the site of the occlusion 16 to treat the particulate, the remaining particulate is broken down further into an aggregate. The particulate and aggregate are similar in size to red blood cells. The size of the aggregate is such that the aggregate is easily discharged from the body through conventional ways or simply dissolves into the blood stream. A conventional way of discharging the aggregate from the body includes transferring the aggregate through the blood stream to the kidney where the aggregate is excreted as bodily waste. The combination effects of the transverse vibrations of the ultrasonic probe 15 with the pharmacological agent provides for ablation of the occlusion 16.

A significant advantage of the present invention is that the ultrasonic medical device 11 physically destroys and removes the material comprising the occlusion 16 (especially adipose or other high water content tissue) through the mechanism of non-thermal cavitation. In a preferred embodiment of the present invention, the occlusion 16 comprises a biological material. In a preferred embodiment of the present invention, the occlusion 16 is a vascular occlusion 16. Cavitation is a process in which small voids are formed in a surrounding fluid through the rapid motion of the ultrasonic probe 15 and the voids are subsequently forced to compress. The compression of the voids creates a wave of acoustic energy which acts to dissolve the matrix binding together the occlusion 16, while having no damaging effects on healthy tissue. The ultrasonic energy source 99 provides a low power electric signal of approximately 2 watts to the transducer, which then transforms the electric signal into acoustic energy. Longitudinal motion created within the transducer is converted into a standing transverse wave along the portion of the longitudinal axis of the ultrasonic probe 15, which generates acoustic energy in the surrounding medium through cavitation. The acoustic energy dissolves the matrix of the occlusion 16.

The ultrasonic energy produced by the ultrasonic probe 15 is in the form of very intense, high frequency sound vibrations that result in physical reactions in the water molecules within a body tissue or surrounding fluids in proximity to the ultrasonic probe 15. These reactions ultimately result in a process called "cavitation," which can be thought of as a form of cold (i.e., non-thermal) boiling of the water in the body tissue, such that microscopic voids are rapidly created and destroyed in the water creating cavities in their wake. As surrounding water molecules rush in to fill the cavity created by the collapsed voids, they collide with each other with great force. Cavitation results in shock waves running outward from the collapsed voids which can wear away or destroy material such as surrounding tissue in the vicinity of the ultrasonic probe 15.

The removal of the occlusion 16 by cavitation and the treatment of the pharmacological agent also provides the ability to remove large volumes of material comprising the occlusion 16 with the small diameter ultrasonic probe 15, while not affecting healthy tissue. The use of the pharmacological agent and cavitation as the mechanism for destroying the occlusion 16 allows the present invention to destroy and remove the material comprising the occlusion 16 within a range of temperatures of about ±7° C. from normal body temperature. Therefore, complications attendant with the use of thermal destruction or necrosis, such as swelling or edema, as well as loss of elasticity are avoided.

The number of transverse nodes 40 and transverse anti-nodes 42 occurring along the longitudinal axis of the ultrasonic probe 15 is modulated by changing the frequency of energy supplied by the ultrasonic energy source 99. The exact frequency, however, is not critical and for the ultrasonic probe 15, the ultrasonic energy source 99 run at, for example, about 20 kHz is generally sufficient to create an effective number of occlusion destroying transverse anti-nodes 42 along the longitudinal axis of the ultrasonic probe 15. The low frequency requirements of the present invention is a further advantage in that the low frequency requirement leads to less damage to healthy tissue. Those skilled in the art understand it is possible to adjust the dimensions of the ultrasonic probe 15, including diameter, length and distance to the ultrasonic energy source 99, in order to affect the number and spacing of the transverse nodes 40 and transverse anti-nodes 42 along a portion of the longitudinal axis of the ultrasonic probe 15.

The present invention allows the use of ultrasonic energy to be applied to occlusions 16 selectively, because the ultrasonic probe 15 conducts energy across a frequency range from about 20 kHz through about 80 kHz. The amount of ultrasonic energy to be applied to a particular treatment site is a function of the amplitude and frequency of vibration of the ultrasonic probe 15. In general, the amplitude or throw rate of the energy is in the range of about 25 microns to about 250 microns, and the frequency in the range of about 20 kHz to about 80 kHz. In a preferred embodiment of the present invention, the frequency of ultrasonic energy is from about 20 kHz to about 35 kHz. Frequencies in this range are specifically destructive of occlusions 16 including, but not limited to, hydrated (water-laden) tissues such as endothelial tissues, while substantially ineffective toward high-collagen connective tissue, or other fibrous tissues including, but not limited to, vascular tissues, epidermal, or muscle tissues.

The amount of cavitation energy to be applied to a particular site requiring treatment is a function of the amplitude and frequency of vibration of the ultrasonic probe 15, the longitudinal length of the ultrasonic probe 15, the geometry at the distal end 24 of the ultrasonic probe 15, the proximity of the ultrasonic probe 15 to the occlusion 16, and the degree to which the length of the ultrasonic probe 15 is exposed to the occlusion 16. Reducing the amount of energy from the ultrasonic source can reduce the amount of damage to healthy tissue.

In a preferred embodiment of the present invention, the transducer transmits ultrasonic energy from the ultrasonic energy source 99 to the longitudinal axis of the ultrasonic probe 15 to oscillate the ultrasonic probe 15 in a direction transverse to its longitudinal axis. In a preferred embodiment of the present invention, the transducer is a piezoelectric transducer that is coupled to the ultrasonic probe 15 to enable transfer of ultrasonic excitation energy and cause the ultrasonic probe 15 to oscillate in the transverse direction relative to the longitudinal axis. In an alternative embodiment of the present invention, a magneto-strictive transducer may be used for transmission of the ultrasonic energy.

In a preferred embodiment of the present invention, the pharmacological agent is tissue plasminogen activator (tPA). tPA is a thrombolytic agent that breaks up or dissolves blood clots. tPA has been approved by the Food and Drug Administration since 1996 for the treatment of stroke and heart attack. tPA acts in a two stage process to dissolve fibrin clots that may be found in a vasculature of the body. Fibrin can be split up by plasmin, where a multitude of plasmin molecules can diffuse through aqueous channels in the fibrin clot to cut the connector rods that comprise the fibrin. In order to form plasmin, tPA binds to a component of the clot called fibrin and activates plasminogen to form plasmin.

Plasmin degrades components of the clot and other proteins that promote the blood clotting.

There are several other pharmacological agents that treat occlusions 16 and can be used for the present invention. Antiplatelet agents prevent a formation of blood platelets, a collection of small blood cells having a disc shape. Blood platelets are an important component to the blood clotting process with the blood platelets collecting to form a blood clot. Aspirin is the most common antiplatelet agent that is used to prevent clots. Aspirin is also known as a nonsteroidal anti-inflammatory agent that stops blood platelets from sticking together and forming a blood clot. Glycoprotein inhibitors are potent blood thinning agents that block platelets and include abciximab, Eptifibatide, tirofiban and lamifiban. Thienopyrindines are oral platelet inhibitors and include clopidogrel and ticlopidine. Anticoagulants, including heparin and warfarin are also used to help thin blood. Lysing agents work to break up or disintegrate the occlusion 16. Dipyridamole is similar to aspirin in that it inhibits platelet adhesion, and thus tends to prevent the vascular thrombosis of heart attacks and strokes. Hirudin is an anticoagulant peptide whose anticoagulant activity comes from the chemical ability to inhibit thrombus formation. Urokinase and streptokinase, thrombolytic agents similar to tPA, work by activating the body's own fibrinolytic system by activating the production of plasmin from plasminogen. Those skilled in the art will recognize there are other pharmacological agents known in the art that can be used to treat occlusions that are within the spirit and scope of the present invention.

The ultrasonic probe 15 is designed to have the cross section with a small profile, which also allows the ultrasonic probe 15 to flex along its length, thereby allowing the ultrasonic probe 15 to be used in a minimally invasive manner. A significant feature of the present invention resulting from the transversely generated energy is the retrograde movement of biological material, e.g., away from the probe tip 9 and along the longitudinal axis of the ultrasonic probe 15.

In a preferred embodiment of the present invention, the ultrasonic probe 15 has a small diameter. In a preferred embodiment of the present invention, the diameter of the ultrasonic probe 15 gradually decreases from the proximal end 31 to the distal end 24. In an embodiment of the present invention, the diameter of the distal end 24 of the ultrasonic probe 15 is about 0.004 inches. In another embodiment of the present invention, the diameter of the distal end 24 of the ultrasonic probe 15 is about 0.015 inches. In other embodiments of the present invention, the diameter of the distal end 24 of the ultrasonic probe 15 varies between about 0.003 inches and about 0.025 inches. Those skilled in the art will recognize an ultrasonic probe 15 can have a diameter at the distal end 24 smaller than about 0.003 inches, larger than about 0.025 inches, and between about 0.003 inches and about 0.025 inches and be within the spirit and scope of the present invention.

In an embodiment of the present invention, the diameter of the proximal end 31 of the ultrasonic probe 15 is about 0.012 inches. In another embodiment of the present invention, the diameter of the proximal end 31 of the ultrasonic probe 15 is about 0.025 inches. In other embodiments of the present invention, the diameter of the proximal end 31 of the ultrasonic probe 15 varies between about 0.003 inches and about 0.025 inches. Those skilled in the art will recognize the ultrasonic probe 15 can have a diameter at the proximal end 31 smaller than about 0.003 inches, larger than about 0.025 inches, and between about 0.003 inches and about 0.025 inches and be within the spirit and scope of the present invention.

In an embodiment of the present invention, the diameter of the ultrasonic probe 15 is approximately uniform from the proximal end 31 to the distal end 24 of the ultrasonic probe 15. In another embodiment of the present invention, the diameter of the ultrasonic probe 15 gradually decreases from the proximal end 31 to the distal end 24. In an embodiment of the present invention, the ultrasonic probe 15 may resemble a wire. In an embodiment of the present invention, the gradual change of the diameter from the proximal end 31 to the distal end 24 occurs over the at least one diameter transitions 82 with each diameter transition 82 having an approximately equal length. In another embodiment of the present invention, the gradual change of the diameter from the proximal end 31 to the distal end 24 occurs over a plurality of diameter transitions 82 with each diameter transition 82 having a varying length. The diameter transition 82 refers to a section where the diameter varies from a first diameter to a second diameter.

The length of the ultrasonic probe 15 of the present invention is chosen so as to be resonant in a transverse mode. In an embodiment of the present invention, the ultrasonic probe 15 is between about 30 centimeters and about 300 centimeters in length. In an embodiment of the present invention, the ultrasonic probe is a wire. Those skilled in the art will recognize an ultrasonic probe can have a length shorter than about 30 centimeters and a length longer than about 300 centimeters and be within the spirit and scope of the present invention.

The ultrasonic probe 15 is inserted into a vasculature 44 of the body and may be disposed of after use. In a preferred embodiment of the present invention, the ultrasonic probe 15 is for a single use and on a single patient. In a preferred embodiment of the present invention, the ultrasonic probe 15 is disposable. In another embodiment of the present invention, the ultrasonic probe 15 can be used multiple times.

Figure 5:
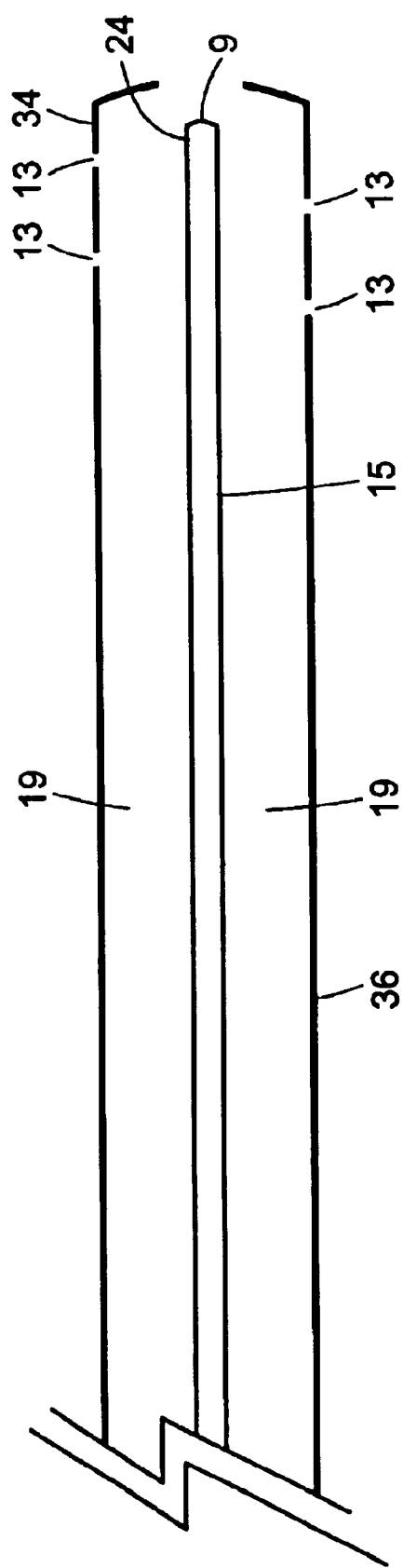
FIG. 5 shows a fragmentary side plan view of a distal end of an ultrasonic probe within a catheter.

FIG. 5 shows a fragmentary side view of the ultrasonic probe 15 within the catheter 36. The ultrasonic probe 15 comprises the distal end 24 and the probe tip 9. The catheter comprises the plurality of fenestrations 13 at the distal end 34 of the catheter 36. In the embodiment of the present invention shown in FIG. 5, the distal end 24 with the probe tip 9 of the ultrasonic probe 15 is within the catheter 36. There is an open area 19 between the ultrasonic probe 15 and the catheter 36. The pharmacological agent is advanced between the open area 19 and moves through the plurality of fenestrations 13.

Figure 6:
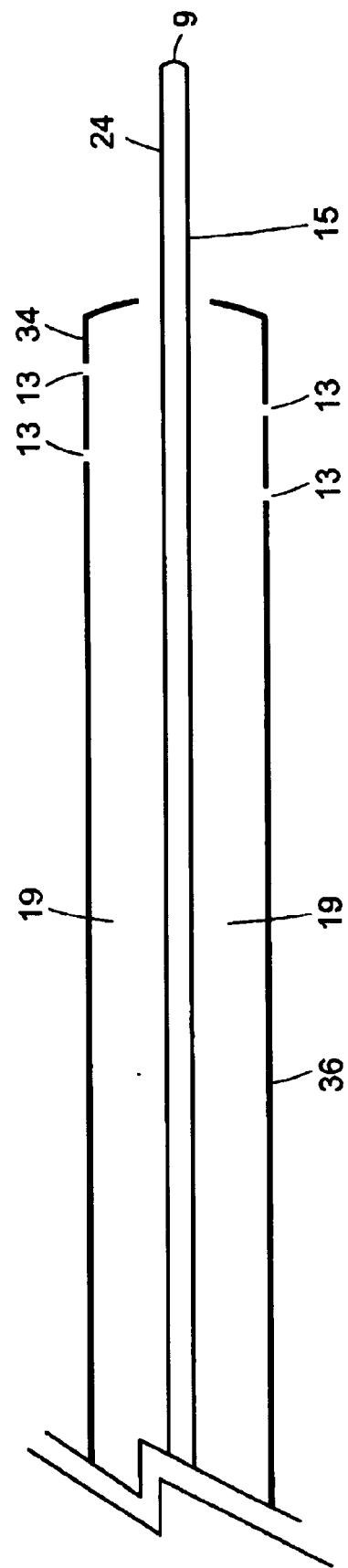
FIG. 6 shows a fragmentary side plan view of a distal end of an ultrasonic probe within a catheter wherein a section of a longitudinal axis of the ultrasonic probe extends beyond a distal end of the catheter.

FIG. 6 shows a fragmentary side view of the ultrasonic probe 15 within the catheter 36 wherein the section of the longitudinal axis of the ultrasonic probe 15 extends past a distal end 34 of the catheter.

The present invention also provides a method of treating an occlusion 16 through a combination of the ultrasonic probe 15 and the pharmacological agent. The ultrasonic probe 15 is inserted into the vasculature 44 of the body and the catheter 36 is delivered over a length of the longitudinal axis of the ultrasonic probe 15 as shown in FIG. 5. In another embodiment of the present invention, the catheter 36 is inserted into the vasculature 44 of the body and the ultrasonic probe 15 is moved within the catheter 36. As the catheter 36 is inserted into the vasculature 44, the placement wings 95 engage the patient's skin to secure the catheter 36. The connecting tube 79 is opened by the one or more valves 97 and a pharmacological agent is released through the catheter 36 into the open area 19 between the ultrasonic probe 15 and the catheter 36. The pharmacological agent engages the occlusion 16. A section of the longitudinal axis of the ultrasonic probe 15 is advanced past a distal end 34 of the catheter as shown in FIG. 6. The section of the longitudinal axis of the ultrasonic probe 15 is exposed to the occlusion 16 and the ultrasonic source 99 is activated. In one embodiment of the present invention, the section of the longitudinal axis of the ultrasonic probe 15 is exposed by pushing the section of the longitudinal axis of the ultrasonic probe 15 past the distal end 34 of the catheter 36. In another embodiment of the present invention, the section of the longitudinal axis of the ultrasonic probe 15 is exposed by pulling back on the catheter 36. The pharmacological agent enhances an occlusion treating effect of the ultrasonic probe 15 by working in combination with the ultrasonic probe 15 at the site of the occlusion 16 and downstream of the site of the occlusion 16. The combination of the ultrasonic energy from the ultrasonic probe 15 and the pharmacological agent breaks up the occlusion 16 into the particulate that is carried by the blood stream downstream of the site of the occlusion 16. Sizes of the particulate vary from a smallest size that can be easily absorbed and discharged through the body in conventional ways to a size that may have a risk of a subsequent occlusion 16 formation downstream. The combination of the ultrasonic energy from the ultrasonic probe 15 and the pharmacological agent further breaks up the particulate into an aggregate downstream of the particulate. The size of the aggregate is such that the aggregate is easily discharged from the body in conventional ways or is simply dissolved into the blood stream.

The use of the pharmacological agent in conjunction with the ultrasonic probe 15 is a reliable method of effecting removing the occlusion 16 that is also cost effective. In addition to suffering from complications and not being effective when used alone, the use of pharmacological agents alone requires a large quantity of the pharmacological agent to treat the occlusion 16. The present invention requires a lower quantity of the pharmacological agent due to the combinational effects of the pharmacological agent with the ultrasonic probe 15. The lower amount of the pharmacological agent translates into a more cost effective solution that also includes the added benefit of more effective occlusion 16 removal.

The present invention also provides a method of removing an occlusion 16 by moving the ultrasonic probe 15 through the vasculature 44 to the site of the occlusion 16 and releasing a pharmacological agent in the vasculature 44. An ultrasonic energy source is activated and the longitudinal axis of the ultrasonic-probe 15 is vibrated in the transverse direction. The pharmacological agent enhances an occlusion destroying effect of the ultrasonic probe 15. The pharmacological agent engages the occlusion 16 and moves downstream of the site of the occlusion 16 with the particulate. While moving downstream, the pharmacological agent continues to break up the particulate to the aggregate.

The present invention provides an apparatus and a method for more completely removing an occlusion 16 by using a pharmacological agent in conjunction with an ultrasonic probe 15 to enhance an occlusion treating effect of the ultrasonic probe 15. The pharmacological agent is delivered through a plurality of fenestrations 13 of the catheter 36 and treats the occlusion 16 at the site of the occlusion 16 and continues to travel downstream of the site of the occlusion 16. The combination of the pharmacological agent and the transverse vibrations of the ultrasonic probe 15 breaks up the occlusion 16 into a particulate downstream of the site of the occlusion 16 and continues to treat the particulate and breaks up the particulate into an aggregate to a size that is easily removed from the body in conventional ways. The present invention provides an apparatus and a method for more completely removing an occlusion that is safe, simple, efficient, effective, user-friendly, reliable and cost effective.

All patents, patent applications, and published references cited herein are hereby incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. An ultrasonic medical device comprising:
   an ultrasonic probe having a proximal end, a distal end and a longitudinal axis therebetween; and
   a catheter surrounding a length of the longitudinal axis of the ultrasonic probe,
   wherein the catheter delivers a pharmacological agent to treat an occlusion and enhance an occlusion treating effect of the ultrasonic probe to ablate the occlusion.

2. The device of claim 1 wherein the occlusion comprises a biological material.

3. The device of claim 1 wherein the pharmacological agent is localized at the occlusion.

4. The device of claim 1 wherein the pharmacological agent softens the occlusion.

5. The device of claim 1 wherein a section of the longitudinal axis of the ultrasonic probe is located outside of a distal end of the catheter.

6. The device of claim 1 wherein the pharmacological agent is a tissue plasminogen activator.

7. The device of claim 1 wherein the pharmacological agent is selected from a group consisting of thrombolytic agents, antiplatelet drugs, lysing agents, anticoagulants, and similar agents that treat the occlusion.

8. The device of claim 1 wherein the pharmacological agent is selected from a group consisting of aspirin, dipyridamole, glycoprotein inhibitors, thienopyrindines, clopidogrel, hirudin, urokinase, streptokinase, heparin, warfarin and similar agents that treat the occlusion.

9. The device of claim 1 wherein the catheter has an at least one fenestration along a length of the catheter.

10. The device of claim 1 wherein the catheter has a plurality of fenestrations along a length of the catheter.

11. The device of claim 1 wherein the pharmacological agent moves through a plurality of fenestrations located along a length of the catheter.

12. The device of claim 1 wherein the pharmacological agent moves through an opening at a distal end of the catheter.

13. The device of claim 1 wherein a diameter of the ultrasonic probe is approximately uniform along the longitudinal axis of the ultrasonic probe.

14. The device of claim 1 wherein a diameter of the ultrasonic probe varies from the proximal end of the ultrasonic probe to the distal end of the ultrasonic probe.

15. The device of claim 1 wherein a cross section of the ultrasonic probe has a small profile.

16. The device of claim 1 wherein a length and a cross section of the ultrasonic probe are sized to support a transverse ultrasonic vibration with a plurality of transverse nodes and transverse anti-nodes along a portion of the longitudinal axis of the ultrasonic probe wherein more than one of the plurality of transverse anti-nodes are in communication with the occlusion.

17. The device of claim 1 wherein the ultrasonic probe is for a single use on a single patient.

18. The device of claim 1 wherein the ultrasonic probe is disposable.

19. The device of claim 1 wherein the ultrasonic probe has a stiffness that gives the ultrasonic probe a flexibility to be articulated in a vasculature.

20. An ultrasonic medical device for ablating an occlusion comprising:
an elongated, flexible probe having a proximal end, a distal end and a longitudinal axis therebetween; and
a catheter surrounding a length of the longitudinal axis of the elongated, flexible probe,
wherein a pharmacological agent moves through the catheter to enhance an effect of a transverse ultrasonic vibration of the elongated, flexible probe to ablate the occlusion.

21. The device of claim 20 wherein the occlusion comprises a biological material.

22. The device of claim 20 wherein the pharmacological agent softens the occlusion.

23. The device of claim 20 wherein the elongated, flexible probe supports the transverse ultrasonic vibration along a portion of the longitudinal axis of the elongated, flexible probe to remove the occlusion.

24. The device of claim 20 wherein the transverse ultrasonic vibration of the elongated, flexible probe produces a plurality of transverse nodes and transverse anti-nodes along a portion of the longitudinal axis of the elongated, flexible probe.

25. The device of claim 24 wherein the transverse anti-nodes are points of a maximum transverse energy along a portion of the longitudinal axis of the elongated, flexible probe.

26. The device of claim 24 wherein the transverse anti-nodes cause a cavitation in a medium in communication with the elongated, flexible probe.

27. The device of claim 24 wherein more than one of the plurality of transverse anti-nodes are in communication with the occlusion.

28. The device of claim 20 wherein the pharmacological agent is a tissue plasminogen activator.

29. The device of claim 20 wherein the pharmacological agent is selected from a group consisting of thrombolytic agents, antiplatelet drugs, lysing agents, anticoagulants, and similar agents that treat the occlusion.

30. The device of claim 20 wherein the pharmacological agent is selected from a group consisting of aspirin, dipyridamole, glycoprotein inhibitors, thienopyrindines, clopidogrel, hirudin, urokinase, streptokinase, heparin, warfarin and similar agents that treat the occlusion.

31. The device of claim 20 wherein the catheter has an at least one fenestration along a length of the catheter.

32. The device of claim 20 wherein the catheter has a plurality of fenestrations along a length of the catheter.

33. The device of claim 20 wherein the pharmacological agent moves through a plurality of fenestrations located along a length of the catheter.

34. The device of claim 20 wherein the pharmacological agent moves through an opening at a distal end of the catheter.

35. The device of claim 20 wherein a diameter of the elongated, flexible probe is approximately uniform along the longitudinal axis of the elongated, flexible probe.

36. The device of claim 20 wherein a diameter of the elongated, flexible probe varies from the proximal end of the elongated, flexible probe to the distal end of the elongated, flexible probe.

37. The device of claim 20 wherein the elongated, flexible probe has a stiffness that gives the elongated, flexible probe a flexibility to be articulated in a vasculature.

38. A method of treating an occlusion comprising:
inserting an ultrasonic probe in a vasculature of a body;
delivering a catheter over a length of a longitudinal axis of the ultrasonic probe;
releasing a pharmacological agent through the catheter;
exposing a section of the longitudinal axis of the ultrasonic probe to the occlusion; and
activating an ultrasonic source to provide an ultrasonic energy to the ultrasonic probe wherein the pharmacological agent enhances an occlusion treating effect of the ultrasonic probe by working in combination with the ultrasonic probe at a site of the occlusion and downstream of the site of the occlusion.

39. The method of claim 38 wherein the occlusion comprises a biological material.

40. The method of claim 38 wherein the pharmacological agent is localized at the occlusion.

41. The method of claim 38 wherein the pharmacological agent engages the occlusion and moves downstream of the site of the occlusion.

42. The method of claim 38 wherein the combination of the ultrasonic energy from the ultrasonic probe and the pharmacological agent breaks up the occlusion into a particulate downstream of the site of the occlusion.

43. The method of claim 42 wherein the combination of the ultrasonic energy from the ultrasonic probe and the pharmacological agent breaks up the particulate into an aggregate downstream of the site of the occlusion.

44. The method of claim 38 wherein the ultrasonic probe is a wire.

45. The method of claim 38 wherein the ultrasonic probe is moved to a site of the occlusion and remains proximal to the site of the occlusion.

46. The method of claim 38 wherein the pharmacological agent is a tissue plasminogen activator.

47. The method of claim 38 wherein the pharmacological agent is selected from a group consisting of thrombolytic agents, antiplatelet drugs, lysing agents, anticoagulants, and similar agents that treat the occlusion.

48. The device of claim 38 wherein the pharmacological agent is selected from a group consisting of aspirin, dipyridamole, glycoprotein inhibitors, thienopyrindines, clopidogrel, hirudin, urokinase, streptokinase, heparin, warfarin and similar agents that treat the occlusion.

49. The method of claim 38 wherein the catheter has an at least one fenestration along a length of the catheter.

50. The method of claim 38 wherein the catheter has a plurality of fenestrations along a length of the catheter.

51. The method of claim 50 wherein the pharmacological agent moves through the plurality of fenestrations located along the length of the catheter.

52. The method of claim 38 wherein the pharmacological agent moves through an opening at a distal end of the catheter.

53. The method of claim 38 wherein a diameter of the ultrasonic probe is approximately uniform along the longitudinal axis of the ultrasonic probe.

54. The method of claim 38 wherein a diameter of the ultrasonic probe varies from a proximal end of the ultrasonic probe to a distal end of the ultrasonic probe.

55. The method of claim 38 wherein a cross section of the ultrasonic probe has a small profile.

56. The method of claim 38 wherein a length and a cross section of the ultrasonic probe are sized to support a transverse ultrasonic vibration with a plurality of transverse nodes and transverse anti-nodes along a portion of the longitudinal axis of the ultrasonic probe wherein more than one of the plurality of transverse anti-nodes are in communication with the occlusion.

57. The method of claim 38 wherein the ultrasonic probe is for a single use on a single patient.

58. The method of claim 38 wherein a section of the longitudinal axis of the ultrasonic probe is exposed by moving the section of the longitudinal axis of the ultrasonic probe past a distal end of the catheter.

59. The method of claim 38 wherein the section of the longitudinal axis of the ultrasonic probe is exposed by pulling back on the catheter.

60. The method of claim 38 wherein the ultrasonic probe is disposable.

61. A method of removing an occlusion comprising:
   moving an elongated, flexible probe through a vasculature to a site of the occlusion;
   releasing a pharmacological agent in the vasculature having the occlusion to enhance an occlusion removing effect of the elongated, flexible probe; and
   activating an ultrasonic energy source to vibrate a longitudinal axis of the elongated, flexible probe in a transverse direction to remove the occlusion.

62. The method of claim 61 wherein a catheter surrounds a length of the longitudinal axis of the elongated, flexible probe.

63. The method of claim 61 wherein a section of the longitudinal axis of the elongated, flexible probe is exposed to the occlusion.

64. The method of claim 61 wherein the pharmacological agent engages an occlusion and moves downstream from the site of the occlusion.

65. The method of claim 61 wherein a combination of an ultrasonic energy from the elongated, flexible probe and the pharmacological agent breaks up the occlusion into a particulate downstream from the site of the occlusion.

66. The method of claim 61 wherein a combination of an ultrasonic energy from the elongated, flexible probe and the pharmacological agent breaks up a particulate into an aggregate downstream from the site of the occlusion.

67. The method of claim 61 wherein a length and a cross section of the elongated, flexible probe are sized to support a transverse ultrasonic vibration with a plurality of transverse nodes and transverse anti-nodes along a portion of the longitudinal axis of the elongated, flexible probe wherein more than one of the plurality of transverse anti-nodes are in communication with the occlusion.

68. The method of claim 61 wherein the elongated, flexible probe has a stiffness that gives the elongated, flexible probe a flexibility to be articulated in the vasculature.

* * * * *

UNITED STATES PATENT AND TRADEMARK OFFICE
CERTIFICATE OF CORRECTION

| | |
|---|---|
| PATENT NO. | : 6,733,451 B2 |
| DATED | : May 11, 2004 |
| INVENTOR(S) | : Rabiner et al. |

It is certified that error appears in the above-identified patent and that said Letters Patent is hereby corrected as shown below:

<u>Title page,</u>
Item [57], ABSTRACT, should read:
-- An apparatus and a method of using an ultrasonic probe with a pharmacological agent to enhance an occlusion treating effect of the ultrasonic probe to effectively remove an occlusion. The pharmacological agent is released through a catheter to treat the occlusion and enhance an effect of a transverse ultrasonic vibration of the ultrasonic probe to effectively remove the occlusion. The pharmacological agent continues to travel downstream of the site of the occlusion and work in conjunction with the ultrasonic probe to reduce the occlusion to a size that can easily be removed from the body naturally in order to prevent reformation of the occlusion and other health risks.

<u>Column 16,</u>
Line 23, should read:

1.   An ultrasonic medical device comprising:
     an ultrasonic probe having a proximal end, a distal end and a longitudinal axis therebetween; and
     a catheter surrounding a length of the longitudinal axis of the ultrasonic probe, wherein the catheter delivers a pharmacological agent to treat an occlusion and enhance an occlusion treating effect of the ultrasonic probe vibrating in a transverse mode to ablate the occlusion along a section of the longitudinal axis and probe a tip.

<u>Column 17,</u>
Line 17, should read:
20.  An ultrasonic medical device for ablating an occlusion comprising:
     an elongated, flexible probe having a proximal end, a distal end and a longitudinal axis therebetween; and
     a catheter surrounding a length of the longitudinal axis of the elongated, flexible probe, wherein a pharmacological agent moves through the catheter to enhance an effect of a transverse ultrasonic vibration of the elongated, flexible probe to ablate the occlusion along a section of the longitudinal axis and a probe tip.

UNITED STATES PATENT AND TRADEMARK OFFICE
CERTIFICATE OF CORRECTION

PATENT NO. : 6,733,451 B2
DATED : May 11, 2004
INVENTOR(S) : Rabiner et al.

It is certified that error appears in the above-identified patent and that said Letters Patent is hereby corrected as shown below:

38. A method of treating an occlusion comprising:
inserting an ultrasonic probe in a vasculature of a body;
delivering a catheter over a length of a longitudinal axis of the ultrasonic probe;
releasing a pharmacological agent through the catheter;
exposing a section of the longitudinal axis of the ultrasonic probe to the occlusion; and activating an ultrasonic source to provide an ultrasonic energy to the ultrasonic probe wherein the pharmacological agent enhances an occlusion treating effect of the ultrasonic probe vibrating in a transverse mode to ablate the occlusion along a section of the longitudinal axis and a probe tip by working in combination with the ultrasonic probe at a site of the occlusion and downstream of the site of the occlusion.

61. A method of moving an occlusion comprising:
moving an elongated, flexible probe through a vasculature to a site of the occlusion, releasing a pharmacological agent in the vasculature having the occlusion to enhance an occlusion removing effect of the elongated, flexible probe; and
activating an ultrasonic energy source to vibrate a longitudinal axis of the elongated, flexible probe in a transverse direction to remove the occlusion along a section of the longitudinal axis and a probe tip.

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO.     : 6,733,451 B2
DATED          : May 11, 2004
INVENTOR(S)    : Rabiner et al.

It is certified that error appears in the above-identified patent and that said Letters Patent is hereby corrected as shown below:

Title page,
Item [57], ABSTRACT, should read:
-- An apparatus and a method of using an ultrasonic probe with a pharmacological agent to enhance an occlusion treating effect of the ultrasonic probe to effectively remove an occlusion. The pharmacological agent is released through a catheter to treat the occlusion and enhance an effect of a transverse ultrasonic vibration of the ultrasonic probe to effectively remove the occlusion. The pharmacological agent continues to travel downstream of the site of the occlusion and work in conjunction with the ultrasonic probe to reduce the occlusion to a size that can easily be removed from the body naturally in order to prevent reformation of the occlusion and other health risks. --

Column 16,
Line 23, should read:

1. An ultrasonic medical device comprising:
   an ultrasonic probe having a proximal end, a distal end and a longitudinal axis therebetween; and
   a catheter surrounding a length of the longitudinal axis of the ultrasonic probe, wherein the catheter delivers a pharmacological agent to treat an occlusion and enhance an occlusion treating effect of the ultrasonic probe vibrating in a transverse mode to ablate the occlusion along a section of the longitudinal axis and a probe a tip.

Column 17,
Line 17, should read:
20. An ultrasonic medical device for ablating an occlusion comprising:
   an elongated, flexible probe having a proximal end, a distal end and a longitudinal axis therebetween; and
   a catheter surrounding a length of the longitudinal axis of the elongated, flexible probe, wherein a pharmacological agent moves through the catheter to enhance an effect of a transverse ultrasonic vibration of the elongated, flexible probe to ablate the occlusion along a section of the longitudinal axis and a probe tip.

UNITED STATES PATENT AND TRADEMARK OFFICE
CERTIFICATE OF CORRECTION

PATENT NO. : 6,733,451 B2
DATED : May 11, 2004
INVENTOR(S) : Rabiner et al.

It is certified that error appears in the above-identified patent and that said Letters Patent is hereby corrected as shown below:

38. A method of treating an occlusion comprising:
inserting an ultrasonic probe in a vasculature of a body;
delivering a catheter over a length of a longitudinal axis of the ultrasonic probe;
releasing a pharmacological agent through the catheter;
exposing a section of the longitudinal axis of the ultrasonic probe to the occlusion; and activating an ultrasonic source to provide an ultrasonic energy to the ultrasonic probe wherein the pharmacological agent enhances an occlusion treating effect of the ultrasonic probe vibrating in a transverse mode to ablate the occlusion along a section of the longitudinal axis and a probe tip by working in combination with the ultrasonic probe at a site of the occlusion and downstream of the site of the occlusion.

61. A method of removing an occlusion comprising:
moving an elongated, flexible probe through a vasculature to a site of the occlusion; releasing a pharmacological agent in the vasculature having the occlusion to enhance an occlusion removing effect of the elongated, flexible probe; and
activating an ultrasonic energy source to vibrate a longitudinal axis of the elongated, flexible probe in a transverse direction to remove the occlusion along a section of the longitudinal axis and a probe tip.

This certificate supersedes Certificate of Correction issued August 24, 2004.

Signed and Sealed this

Ninth Day of November, 2004

JON W. DUDAS
*Director of the United States Patent and Trademark Office*

UNITED STATES PATENT AND TRADEMARK OFFICE
CERTIFICATE OF CORRECTION

PATENT NO.     : 6,733,451 B2
DATED          : May 11, 2004
INVENTOR(S)    : Rabiner et al.

It is certified that error appears in the above-identified patent and that said Letters Patent is hereby corrected as shown below:

Title page,
Item [57], ABSTRACT, should read:
-- An apparatus and a method of using an ultrasonic probe with a pharmacological agent to enhance an occlusion treating effect of the ultrasonic probe to effectively remove an occlusion. The pharmacological agent is released through a catheter to treat the occlusion and enhance an effect of a transverse ultrasonic vibration of the ultrasonic probe to effectively remove the occlusion. The pharmacological agent continues to travel downstream of the site of the occlusion and work in conjunction with the ultrasonic probe to reduce the occlusion to a size that can easily be removed from the body naturally in order to prevent reformation of the occlusion and other health risks. --

Column 16,
Line 23, should read:

1.   An ultrasonic medical device comprising:
     an ultrasonic probe having a proximal end, a distal end and a longitudinal axis therebetween; and
     a catheter surrounding a length of the longitudinal axis of the ultrasonic probe, wherein the catheter delivers a pharmacological agent to treat an occlusion and enhance an occlusion treating effect of the ultrasonic probe vibrating in a transverse mode to ablate the occlusion along a section of the longitudinal axis and a probe tip.

Column 17,
Line 17, should read:
20.  An ultrasonic medical device for ablating an occlusion comprising:
     an elongated, flexible probe having a proximal end, a distal end and a longitudinal axis therebetween; and
     a catheter surrounding a length of the longitudinal axis of the elongated, flexible probe, wherein a pharmacological agent moves through the catheter to enhance an effect of a transverse ultrasonic vibration of the elongated, flexible probe to ablate the occlusion along a section of the longitudinal axis and a probe tip.

UNITED STATES PATENT AND TRADEMARK OFFICE
CERTIFICATE OF CORRECTION

PATENT NO. : 6,733,451 B2
DATED : May 11, 2004
INVENTOR(S) : Rabiner et al.

It is certified that error appears in the above-identified patent and that said Letters Patent is hereby corrected as shown below:

38. A method of treating an occlusion comprising:
inserting an ultrasonic probe in a vasculature of a body;
delivering a catheter over a length of a longitudinal axis of the ultrasonic probe;
releasing a pharmacological agent through the catheter;
exposing a section of the longitudinal axis of the ultrasonic probe to the occlusion; and activating an ultrasonic source to provide an ultrasonic energy to the ultrasonic probe wherein the pharmacological agent enhances an occlusion treating effect of the ultrasonic probe vibrating in a transverse mode to ablate the occlusion along a section of the longitudinal axis and a probe tip by working in combination with the ultrasonic probe at a site of the occlusion and downstream of the site of the occlusion.

61. A method of removing an occlusion comprising:
moving an elongated, flexible probe through a vasculature to a site of the occlusion; releasing a pharmacological agent in the vasculature having the occlusion to enhance an occlusion removing effect of the elongated, flexible probe; and
activating an ultrasonic energy source to vibrate a longitudinal axis of the elongated, flexible probe in a transverse direction to remove the occlusion along a section of the longitudinal axis and a probe tip.

This certificate supersedes Certificate of Correction issued August 24, 2004 and November 9, 2004.

Signed and Sealed this

Twenty-ninth Day of March, 2005

JON W. DUDAS
*Director of the United States Patent and Trademark Office*